United States Patent [19]

Liston

[11] 4,046,702
[45] * Sept. 6, 1977

[54] LUBRICATING OIL COMPOSITION

[75] Inventor: Thomas V. Liston, San Rafael, Calif.

[73] Assignee: Chevron Research Company, San Francisco, Calif.

[*] Notice: The portion of the term of this patent subsequent to May 4, 1993, has been disclaimed.

[21] Appl. No.: 655,659

[22] Filed: Feb. 5, 1976

[51] Int. Cl.$^2$ ............................................. C10M 1/38
[52] U.S. Cl. ................................... 252/33.4; 252/33; 252/47.5
[58] Field of Search ....................... 252/33, 33.4, 47.5

[56] References Cited

U.S. PATENT DOCUMENTS 3,954,639    5/1976    Liston .................................. 252/47.5

*Primary Examiner*—C. Davis
*Attorney, Agent, or Firm*—C. J. Tonkin; L. L. Priest

[57] ABSTRACT

A lubricating oil composition of improved rust-inhibitory capability contains a small amount of a sulfated alcohol having a molecular weight in the range of 500 to 5,000 which is prepared by reacting an aliphatic alcohol or a phenol with ethylene oxide or propylene oxide or mixtures thereof to form a polyoxyalkenylated alcohol which is treated with sodium hydride, potassium, sodium, sodium methoxide, potassium methoxide or potassium tert-butoxide and then is sulfated by treating with chlorosulfonic acid.

6 Claims, No Drawings

LUBRICATING OIL COMPOSITION

BACKGROUND OF THE INVENTION

Automotive lubricating oils are employed both for lubrication and as a vehicle which serve to protect the lubricated surfaces against such deleterious processes as rust and corrosion, and the deposition of varnish. An important means for inhibiting rust and corrosion involves the rapid neutralization of acidic products of oil and fuel oxidation by lubricating oil additives or combinations of additives.

The sulfates have been taught as high-foaming detergents for use in aqueous cleansing solutions, e.g., Weil et al, Journal of the American Oil Chemist Society 36, pages 241 (1959) and 34, page 516 (1957).

The use of sulfates or polyoxyalkylenated alcohols or polyoxyalkenylated phenols or the sulfate salts thereof is disclosed in copending Ser. No. 451,258, filed March 14, 1974, now U.S. Pat. No. 3,954,639.

SUMMARY OF THE INVENTION

The lubricating oil composition of this invention is capable of rapid neutralization of aqueous acid and greater rust protection for internal combustion engines. This improved composition consists of an oil and a rust-inhibiting amount of a sulfate of an oxyalkenylated $C_1-C_{40}$ alcohol or phenol or the sulfate salts thereof, wherein the sulfate has a total molecular weight of about 500–5,000.

DESCRIPTION OF PREFERRED EMBODIMENTS

The improved lubricating oil composition of the present invention consists of an oil of lubricating viscosity and a rustinhibiting amount of a sulfate of a polyoxyalkylenated alcohol or phenol is prepared by (1) reacting an aliphatic alcohol having from 1 to 20 carbon atoms, from 0 to 10 amino groups, and from 1 to 10 hydroxy groups or a phenol or $C_1C_{20}$ alkylphenol with ethylene oxide or propylene oxide or mixtures thereof to form a polyoxyalkylenated alcohol or phenol; (2) treating the polyoxyalkylenated alcohol or polyoxyalkylenated phenol with sodium, sodium methoxide, potassium, potassium methoxide or potassium tert-butoxide; and (3) sulfating with chlorosulfonic acid to form the sulfated alcohol or phenol.

The oxyalkylenated alcohols and phenols which may be sulfated to produce the auxiliary rust inhibitors of the present invention are derived from hydroxy compounds which are substantially aliphatic compounds such as monohydric and polyhydric alcohols or substantially aromatic (phenolic) compounds such as the substituted phenols. The phenols from which the oxyalkylenated sulfates of this invention may be derived are illustrated by such compounds as phenol, cyclohexylphenol, di(-hydroxyphenyl) disulfide, di(hydroxyphenyl) sulfide, di(hydroxyphenyl) oxide, the condensation product of octylphenol with acetone, benzyl alcohol, the condensation product of heptylphenol with formaldehyde, polyisobutene-substituted phenol having a molecular weight of about 1000, xylene glycol, 4,4'-methylene-bisphenol, didodecylphenol, propylene tetramer-substituted phenol, 2,4-dibutylphenol, 2-chlorophenol, dihydroxybiphenyl, catechol, resorcinol and cresol. Phenol and alkylated phenols having up to 3 alkyl substituents are preferred. Each of the alkyl substituents may contain from 1 to 100, or more, carbon atoms.

The alcohol from which the oxyalkylenated sulfates may be derived is a $C_1-C_{40}$ aliphatic alcohol, preferably an alkanol containing about 1 to 20 carbon atoms and 0 to 10 nitrogen atoms, e.g., amino-alkanols. They may be monohydric alcohols such as methanol, ethanol, iso-octanol, dodecanol, cyclohexanol, cyclopentanol, neopentyl alcohol, isobutyl alcohol, 2-methylcyclohexanol, beta-chloroethanol, monomethyl ether of ethylene glycol, monobutyl ether of ethylene glycol, monopropyl ether of diethylene glycol, monodecyl ether of triethylene glycol, monooleate of ethylene glycol, monostearate of diethylene glycol, sec-pentyl alcohol, tert-butyl alcohol, bromo-decanol, nitrooctadecanol, amino ethanol, and dioleate of glycerol. The polyhydric alcohols contain from 2 to about 10 hydroxy groups and are illustrated by such polyols as ethylene glycol, diethylene glycol, triethylene glycol, tetraethylene glycol, dipropylene glycol, tripropylene glycol, dibutylene glycol, tributylene glycol, and other alkylene glycols in which the alkylene radical contains from 2 to about 8 carbon atoms. Other useful polyhydric alcohols are illustrated by glycerol, monooleate of glycerol, monostearate of glycerol, monomethylether of glycerol, pentaerythritol, 9,10-dihydroxy stearic acid, 1,2-butanediol, 2,3-hexanediol, pinacol, erythritol, arabitol, sorbitol, mannitol, and 1,2-cyclohexanediol.

The amino-alcohols contain about 1–10 nitrogen atoms including amino-alkylene, and amino-arylene-substituted alcohols. They are exemplified by amino-ethanol, 3-amino-ethylpentanol, di(hydroxy ethyl) amine, p-aminophenol, tri(hydroxy propyl) amine, N-hydroxyethyl ethylene diamine, N,N,N'N'-tetrahydroxy trimethylene diamine, and N,N,N'N'-tetrahydroxyethyl ethylenediamine. Preferred amino-alcohols are amino-alkanols which contain 1–4 hydroxy groups, 1–10 nitrogen atoms, and about 1–20 carbon atoms.

The preferred sulfates are derived from polyoxyalkylenated alcohols which before oxyalkylenation contain from 1 to about 20 carbon atoms. For the most part, polyoxyalkylene alcohols having up to about 150 oxyalkylene radicals in which the alkylene contains from 2 to about 8 carbon atoms are preferred. The polyoxyalkylene alcohol or phenol may be a polyoxyethylene, polyoxypropylene or polyoxyethylene/polyoxypropylene copolymer, such as the polyoxyethylene/polyoxypropylene block copolymer alcohols, glycols and glycolethers. The number of oxyalkylene units in a given polyoxyalkylene alcohol or phenol varies, but the average total molecular weight of the composition falls in the range of from about 500 to about 5,000 after sulfation.

The polyoxyethylene/polyoxypropylene block copolymers are particularly preferred. Such copolymers are "amphipathic" in that their structure comprises two dissimilar groups, e.g., water solubilizing oxyethylene groups and the more hydrophobic oxypropylene groups. In addition, the compositions of this invention include the anionic sulfate group which is also believed to be hydrophilic. An additional variable arises if we consider that the sulfate may be neutralized as with amine or ammonia. The composition, solubility properties, location, relation and relative percentages of these dissimilar moieties in relation to the overall molecular configuration can serve to determine their relative efficacy as auxiliary inhibitors in rust, corrosion and varnish control, and therefore the preference for a particular sulfate. Although the formation of a haze will, in general, not have a deleterious effect on the lubricating properties of the compounded oil, such haze is considered a source of potential problems such as filter plugging. Consequently, the most preferred sulfates of the present invention are those which at normal concentration levels as auxiliary rust inhibitors do not produce a haze in the fully compounded oil. The most preferred polyoxyalkylene alcohols incorporate about 10–90 weight percent of oxyethylene units and about 90–10 weight percent of oxypropylene units.

The alcohols or phenols are oxyalkylenated or polyoxyalkylenated by means which are well known in the art as by reaction with ethylene oxide and/or propylene oxide. The preferred alcohols are selected from $C_1$–$C_{20}$ alcohols such as butanol, octanol, etc., or alternatively, the hydroxy derivatives of naturally occurring materials such as lauryl, stearyl and myristyl alcohol, or mixtures of these. The preferred phenols are selected from phenol and $C_1$–$C_{20}$ alkyl-substituted phenols, most preferably $C_1$–$C_{17}$ alkyl-substituted phenols.

The most preferred alcohols are $C_2$–$C_{20}$ polyols having about 2 to 4 hydroxy groups, e.g., diols or glycols, glycerols or triols, and such tetrahydric alcohols as pentaerythritol. The particularly preferred auxiliary rust inhibitors in the practice of this invention are sulfates of polyoxyalkylene polyols containing 2-20 carbon atoms before oxyalkylenation and having from 2 to 4 hydroxyl groups and a total molecular weight after sulfation of from about 500 to about 5,000. 1,2-glycols, 1,3-glycols and alpha, omega-glycols are encompassed among the preferred $C_2$–$C_{20}$ polyols. Particularly preferred compositions are selected from the group of polyoxyalkylenated glycol, glycerol, or pentaerythritol having molecular weights of from about 500 to about 5,000.

The preparation of the sulfates finding use in the present invention is by methods which are known in the art. Sulfation consists of placing a $SO_2OH$ group on oxygen. The sulfate is normally prepared from the oxyalkyl or polyoxyalkylene alcohol or phenol by reaction with chlorosulfonic acid. Method of preparation has been described by Kirk-Othmer, Encyclopedia of Chemical Technology, 2nd Ed., Vol. 19, pp. 301-308. The reaction with chlorosulfonic acid is facilitated by prior formation of the sodium or potassium salt of the alcohol or phenol, i.e., the sodium or potassium alcoholate, or by the addition of sodium hydride, sodium, sodium methoxide, potassium, potassium methoxide or potassium tert-butoxide to the alcohol or phenol followed by reaction of the sodium or potassium alcoholate or phenate with chlorosulfonic acid.

Reaction of a sulfating agent with the polyol leads to a sulfated product which is a mixture of mono- and poly-sulfated polyol, e.g., the reaction with polyalkylene glycerol produces mono-, di- and tri-sulfate according to the usual reaction kinetics, and the sulfated product is suitable for use as thus prepared. Alternatively, reaction conditions, i.e., mol ratios of reactants, may be selected so that the mono-sulfate or disulfate, etc., predominates in the sulfated reaction product. For extrinsic reasons, such as solubility in oleaginous compositions, the polysulfate may be preferred, but in general this distinction is not critical.

Normally, the sulfating agent and the alcohol are reacted in a mol ratio of 1:1 to 1/n, or in other words, one equivalent of sulfating agent to from 1 to $n$ equivalents of polyol where $n$ is the number of hydroxy groups per molecule of polyol. The reaction is carried out at a temperature of from about 25° C to about 150° C for a period of from about 1 to about 48 hours.

Examples of these products include the polyoxyethylene/polyoxypropylene block copolymer glycol ammonium mono- or di-sulfate and the polyoxyethylene/polyoxypropylene block copolymer triol based on glycerol ammonium mono- or poly-sulfate, wherein said copolymers contain 0%-40% ethoxy units.

EXAMPLE 1

Polyoxyethylene/polyoxypropylene block copolymer triol based on glycerol having a total molecular weight of about 4,500 and containing about 10–14 weight percent oxyethylene and the remainder oxypropylene groups (112.5 g) was dried by azeotroping for 30 minutes in toluene and stripping to 80° C at 0.5 mm/Hg. The polyol was cooled and 1.05 g of a 57% sodium hydride dispersion in oil was added under nitrogen. The mixture was heated gently to 55°–60° C with stirring. After 60 minutes hydrogen ceased evolving but the reaction was continued for a total of 4 hours. The product was the monosodium salt of the polyoxyalkylene glycerol.

EXAMPLE 2

The product of Example 1 was mixed with 1.7 cc of chlorosulfonic acid and stirred at room temperature for about 12 hours. The product was diluted with cyclohexane filtered and stripped to 85° C at 0.3 mm/Hg. 102.25 g of product polyoxyalkylene sulfate "A" were obtained.

EXAMPLE 3

The product of Example 2, 1.0 g, was blended with 88.0 g of the polyisobutenyl succinimide of triethylene tetramine for 60 minutes at 70°–80° C. A lubricating composition was made by blending this mixture in lubricating oil with carbonated, sulfurized, calcium polypropylene phenate, petroleum sulfonates, and zinc bis(polypropylene phenol) dithiophosphate.

EXAMPLE 4

To a flask was added, under nitrogen, 252.4 g of the dried polyoxyethylene/polyoxypropylene block copolymer of glycerol (about 14% oxyethylene units and having an average molecular weight of about 4,500), 200 cc of iso-octane and 4.7 g of sodium hydride as a 57.2% dispersion in oil. The mixture was warmed to 60° C and stirred from about 6 hours. 7.4 cc of chlorosulfonic acid was added dropwise over a 20-minute interval. The mixture was heated at 64°–70° C for about 4 hours. The dark product was filtered hot, stripped to 80° C and yielded 219 g of black viscous fluid, the di-sulfate. The di-sulfate (1.0 g) was contacted with 85.5 g of an 8% by weight-solution of the polyisobutenyl succinimide of triethylene tetramine in petroleum oil. The resulting composition contained about 1,000 ppm of the product as a salt.

EXAMPLE 5

The polyoxyethylene/polyoxypropylene block copolymer of glycerol of Example 4 was dried by azeotroping with toluene and stripping, and 225.6 g was added to 100 cc of dry iso-octane; 4.85 g of sulfamic acid was then added at 23° C. The mixture was heated to about 2-½ hours. The product was filtered and stripped to 75° C yielding 219.1 g of dark brown viscous fluid, the mono-ammonium sulfate.

EXAMPLE 7

Sulfamic acid (194.2 g) was added to 950 g of the polyoxyethylene/polyoxypropylene block copolymer glycol of 10% oxyethylene units, having an average molecular weight of about 950. The mixture was heated at about 85°–113° C for about 17 hours. The viscous dark fluid product was diluted with toluene, filtered and stripped to yield 1,019 g of the di-ammonium sulfate.

EXAMPLE 8

A $C_{12}$–$C_{15}$ alkanol polyoxyethylenated to the extent of about 9 oxyethylene units (300 g) was dried and mixed with 26.7 g of sulfamic acid at about 90°–95° C for about 23 hours. The product was diluted with toluene, filtered and stripped to 80° C yielding 171.5 g of ammonium sulfate.

EXAMPLE 9

$C_{12}$-alkylphenol polyoxyethylenated to an average of 5.5 ethylene oxide units (239 g) was mixed with 48.55 g of sulfamic acid at 90°–95° C for about 24 hours. The viscous dark product was diluted with toluene, filtered and stripped to 80° C to yield 266.8 g of the ammonium sulfate.

EXAMPLE 10

Polypropylene glycol (average molecular weight about 2,000) was dried by boiling with benzene and stripping. 200 g of the dried glycol was then mixed with 19.42 g of sulfamic acid and heated with stirring to 92°–98° C for about 23 hours. The product was diluted with toluene, filtered and stripped to yield 205.6 g of the di-ammonium sulfate.

EXAMPLE 11

A polyoxyethylene/polyoxypropylene block copolymer glycol (172 g) of 30% oxyethylene units and average molecular weight about 1,720 was stirred with 19.42 g of sulfamic acid for about 9 hours at 95°–100° C. The dark, extremely viscous product was diluted with a volume of toluene and filtered to yield 190.2 g of the di-sulfate after stripping at 90° C.

EXAMPLE 12

13.25 g of the mono-sulfate of polyoxypropylenated glycerol (average molecular weight about 5,300) was mixed with 0.22 g of 2-methyl, 2-amino, 1-propanol with 200 cc of benzene. The ammonium sulfate product was stripped to 80° C and blended at 550 ppm into a lubricating composition containing 8% by weight of polyisobutenyl succinimide of triethylene tetramine.

EXAMPLE 13

10 g of the glycerol mono-sulfate of Example 12 was mixed with 100 cc of toluene and an excess (5.0 g) of triethylamine. The mixture was stirred for 10 minutes and stripped to 100° C under nitrogen. The product triethylammonium sulfate was a clear, brown fluid.

EXAMPLE 14

Polyisobutenyl succinimide of tetraethylene pentamine (450 g of a 50% solution in neutral petroleum oil) was azeotroped with 200 c of xylene for 60 minutes, cooled and added to 50 g of the ammonium sulfate product of Example 9. The mixture was heated to reflux (155° C) for about 2 hours. The amine-exchange reaction product was blended into a lubricating composition.

EXAMPLE 15

800 g of the polyisobutenyl succinimide of triethylene tetramine (i.e., 0.143 mols as 800 g of a neutral petroleum oil solution) was mixed with 500 ml of xylene, 88.80 g of the disulfate of a polyoxyethylene/polyoxypropylene block copolymer glycol having about 10% polyoxyethylene units and an average molecular weight of about 950, and was azeotroped for 2 hours (152° C). The product ammonium sulfate salt was stripped to 150° C.

LUBRICATING COMPOSITIONS

The compounds of the invention may be used singly or in combinations of 2 or more in an oil of lubricating viscosity. The lubricating oil can be any relatively inert and stable fluid of lubricating viscosity. Such lubricating fluids generally have viscosities of 35–50,000 Saybolt Universal Seconds (SUS) at 100° F (38° C). The fluid medium or cil may be derived from either natural or synthetic sources. Included among the natural hydrocarbonaceous oils are paraffin-base, naphthenic-base or mixed-base oils. Synthetic oils include polymers of various olefins, generally of 2 to 6 carbon atoms, alkylated aromatic hydrocarbons, etc. Nonhydrocarbon oils include polyalkylene oxide, carboxylates, phosphates, aromatic ethers, silicons, etc. The preferred media are the hydrocarbonaceous media, both natural and synthetic. Preferred are those hydrocarbonaceous oils having viscosity of about 100–4,000 SUS at 100° F. The compatibility of the additives of the present invention with the lubricating medium is evidenced, among other things, by a lack of haze.

The lubricating oils will be present at 75 or greater percent by weight in the final lubricating composition. In concentrates, however, the oil may be present in 10–75 weight percent. These concentrates are diluted with additional oil prior to being place in service to obtain the requisite concentration.

The polyoxyalkylene sulfates of the present invention are present in the lubricating oil composition in a rust inhibiting amount. A rust inhibiting amount will usually range from about 10 ppm to about 10,000 ppm, and preferably from 50 or 100 ppm to about 5,000 ppm.

A preferred lubricating composition will contain sufficient alkaline earth metal carbonate dispersed in a hydrocarbon oil to provide an alkalinity value of from 0.5 to 100 milligrams of KOH per gram. The alkaline earth metal carbonates are magnesium, calcium and barium carbonates, preferably calcium and barium carbonate. Small amounts of the hydroxide of the metals may also be present, usually not contributing more than about 20% of the alkalinity value from the alkaline earth metal carbonate composition. The alkaline earth metal compounds are not soluble in hydrocarbon media. Therefore, they are invariably dispersed with some type of metal salt dispersant. These dispersants are well known in the art and will be discussed only summarily.

The preferred dispersants are the sulfonate and phenate dispersants. The sulfonates are extensively discussed in U.S. Pat. No. 3,488,284. The organic sulfonates are prepared either from natural or synthetic sources. The natural sulfonates are referred to as mahogany sulfonates and are prepared from petroleum mineral oil fractions and normally have from 25 to 50 carbon atoms per sulfonic acid. Synthetic sources are also employed which are usually alkylated benzenes having from 25 to 50 carbon atoms. The use of the sulfonates and the method of preparing overbased sulfonates is well known, as already indicated by the above patent. Other patents in this field include U.S. Pat. Nos. 3,021,280, 3,256,186, 3,057,896 and 3,312,618.

Another class of dispersant for alkaline earth metal carbonates is the phenate. The phenates are alkylated phenols either individually or polymerized to a low order of from 2 to 5 alkyl phenols, normally bridged with sulfur, alkylene groups, or di(alkylene) amino groups (Mannich bases). The alkyl group on the phenol is normally of at least 8 carbon atoms and usually does not exceed 36 carbon atoms, more usually being in the range of from about 12 to about 30 carbon atoms. The phenoxide in the phenate also contributes to the alkalinity value. The overbased phenates are described in numerous patents such as U.S. Pat. Nos. 3,474,035, 3,429,812, 3,388,063, 3,336,224 and 2,798,852.

Other dispersants which are also employed are the alkaline earth metal alkyl phosphonates and thiophosphonates. The phosphonates will normally contain at least about 30 carbon atoms and may contain as high as 200 carbon atoms, more usually from about 50 to 125 carbon atoms. The overbased phosphonates are described in U.S. Pat. No. 3,312,618.

The alkalinity value of the overbased dispersants will usually be at least 150 and not exceed 500, more usually being in the range of about 200 to 450 mg of KOH/g. The equivalent ratio of base to dispersant will be at least 1 to 1 and more usually at least 1.5 to 1, normally not exceeding about 20 to 1. These compositions are used in a sufficient amount to provide the desired alkalinity value in the final composition. Therefore, the alkaline earth metal carbonate is prepared as a concentrate and then diluted in the lubricating oil medium with the polyoxyalkylene sulfate to provide the desired end composition.

Other known additives are desirably included in the composition. Such additives include rust and corrosion inhibitors, antioxidants, oiliness agents, detergents, dispersants, antiwear agents, viscosity index improvers, and pour point depressants. Usually such individual additives will be present in the range of from about 0%–5% by weight, more generally in the range from about 0%–2% by weight of the total composition. Such typical additional additives found in compositions of the present invention include alkenyl succinimide dispersants, phenolic and aryl amine antioxidants, and zinc dihydrocarbyl dithiophosphates.

EVALUATION

The Neutralization Rate Test (NRT) has been described in U.S. Pat. No. 3,784,474 and Canadian Pat. No. 911,420. The Neutralization Rate Test consists of the neutralization of an acidic aqueous phase with a basic oil phase. The progress of the neutralization is followed with a pH meter by measuring the pH at convenient time intervals. The pH is plotted versus the time. Basic lubricating compositions will neutralize the acid and exhibit a definite point of inflection, usually in the pH range of 3.5 to 6.5, but the time elasped to the point of inflection (TPI) varies widely depending on the presence or absence of a neutralization promoter of the present invention, all other test factors being kept constant.

The time elapsed from the initial mixing of basic oil and acidic aqueous phases to the point of inflection is the TPI and it forms the basis for comparing various oil compositions. In general, in the comparison of the two oil compositions, the one with a low TPI rating (faster acid neutralization) has been found to have greater rust inhibitory capacity than the composition with the higher TPI (slower acid neutralization) all other factors being kept constant. In this test, the rate of stirring and oil viscosity can also affect the rate of neutralization. Typical repeatability is plus or minus 5% of the mean time to point of inflection. The test is regarded as reliable for screening auxiliary rust inhibitors for engine testing, with which it tends to show a partial correlation.

Neutralization Rate Test data is given in Table 1. The acidic aqueous phase consisted of 0.004 HCl. The sulfates of Tables I and II were prepared by reaction of the hydroxy compound with sulfamic acid. The glycerol-sulfates and glycol-sulfates of Tables I and II were prepared from polyoxy-ethylene/polyoxypropylene block copolymer glycerol and glycols respectively. In each case, the percentage of oxyethylenation relative to the total amount of polyoxyalkylenation in the molecule is given. The remainder of the polyoxyalkylene units is in each case polyoxypropylene. The TPI is the minutes to point of inflection in pH versus time curve. The first value is for mono-ammonium sulfate. The second value is for di-ammonium sulfate. The first column of TPI values is for lubricating Composition A consisting of the sulfate and a neutral mineral oil containing 8 weight percent of polyisobutenyl succinimide of triethylene tetramine wherein said polyisobutenyl is of 950 average molecular weight, 40 mM/kg of carbonated, sulfurized, calcium polypropylene phenate, 22 mM/kg of mixed sulfonates (2.35% calcium) and 14.6 mM/kg of zinc bis(polypropylene phenol/dithiophosphate). The TPI data in the last column of Table I corresponds to a Composition B consisting of, in addition to the sulfate, a neutral mineral oil containing 4 weight percent of polyisobutenyl succinimide of tetraethylene pentamine wherein said polyisobutenyl group is of 950 average molecular weight, 30 mM/kg of carbonated, sulfurized, calcium polypropylene phenate, 40 mM/kg of overbased calcium sulfonate, 7 mM/kg of zinc bis(polypropylene phenyl)dithiophosphate, and 11 mM/kg of zinc di($C_4$–$C_6$ alkyl) dithiophosphate.

TABLE I

| | Neutralizatin Rate Test | | | | |
|---|---|---|---|---|---|
| Sulfate | Average MW | % ETO | Concentration Wt. % | TPI[1] Minutes | TPI[2] Minutes |
| None | — | — | — | 200 | 72 |
| Glycerol | 4500 | 14 | 0.1 | 48/57 | 20/22 |
| Glycol | 4000 | 10 | 0.1 | 6/3 | 10/9 |
| Glycol | 3600 | 10 | 0.1 | 26/— | 13 |
| Glycol | 1950 | 10 | 0.1 | 83/116 | 22/21 |
| Glycol | 1050 | 10 | 0.1 | 120/95 | 29/21 |
| Glycol | 2100 | 30 | 0.1 | —/111 | — |
| Glycol | 2000 | 0 | 0.25 | —/73 | — |
| $C_{12}$-alkylphenol | 500 | 100 | 0.25 | 54 | — |

TABLE I-continued

| | Neutralizatin Rate Test | | | | |
|---|---|---|---|---|---|
| Sulfate | Average MW | % ETO | Concentration Wt. % | TPI[1] Minutes | TPI[2] Minutes |
| $C_{12}-C_{15}$ alkanol | 600 | 100 | 0.70 | 23 | — |

Footnotes
[1]Composition A
[2]Composition B

The results of Table I show the remarkable reduction in neutralization times obtained by the introduction of only 1,000 ppm of polyoxyalkylene sulfate into the lubricating composition. The lubricating additives of the present invention also function in lubricating compositions which do not contain succinimide or amine dispersants. For example, a lubricating composition consisting of 8 weight percent of the polyisobutenyl succinate of pentaerythritol instead of the succinimide, but otherwise identical to composition A, gave a TPI of 72 minutes, while the addition of 1,000 ppm of a polyoxyethylene/polyoxypropylene block copolymer glycol-disulfate (10% ETO) gives a TPI of only 54 minutes. Similarly, the addition of 1,000 ppm of the di-sulfate to a lubricating composition identical to Composition A, except for the substitution of 8 weight percent of polybutene-substituted phosphonate for the succinimide, reduced the TPI from 68 minutes to 42 minutes.

The MS Sequence II C Engine Test results of Table II demonstrate that the polyoxyalkylene sulfates are extremely effective rust inhibitors under actual engine service conditions.

In Table II, the first column of average engine rust (AER) refers to compositions containing the inhibitor at the stated ppm in Composition A, while the second column of average engine rust data refers to the inhibitor in Composition B and the third AER column to Composition C. Composition C contains, in addition to sulfate, 4% by weight of the succinimide of Composition B, 5 mM/kg of petroleum sulfonate (2.35% calcium), 60 mM/kg of the phenate of Composition B, 6 mM/kg of zinc bis(polypropylene phenyl)dithiophosphate and 9 mM/kg of zinc di($C_4$-$C_6$ alkyl)dithiophosphate in a SAE 30 Mideast oil.

Average engine rust of 8.4 is considered a passing value in the Sequence II C Engine Test. The polyoxyethylene/polyoxypropylene block copolymer glycol gives results which are markedly inferior (7.2 AER) to the di-sulfated version of the same glycol at the same concentration (8.9 AER).

What is claimed is:

1. A lubricating composition comprising an oil of lubricating viscosity and from 10 to 10,000 parts per million of the sulfated alcohol or phenol, having a molecular weight in the range of 500–5,000, said sulfated alcohol or phenol being prepared by the steps comprising:
   1. reacting (i) an aliphatic alcohol having from 1–20 carbon atoms, from 0 to 10 amino groups and from 1 to 10 hydroxy groups or phenol or a $C_1$ to $C_{20}$ alkyl phenol with (ii) ethylene oxide or propylene oxide or mixtures thereof, to form a polyoxyalkylenated alcohol or phenol,
   2. reacting said polyoxyalkylenated alcohol or phenol with sodium, potassium, sodium hydride, sodium methoxide, potassium methoxide or potassium t-butoxide to form the sodium or potassium salt of said polyoxyalkylenated alcohol or phenol, and
   3. sulfating said sodium or potassium salt of polyoxyalkylenated alcohol or phenol by reaction with chlorosulfonic acid to form said sulfated alcohol.
2. The lubricating composition as defined in claim 1 wherein said sulfated alcohol is:
   1. further contacted with a basic amine compound selected from ammonia, a primary or secondary alkyl monoamine, an alkanol amine, an alkylenepolyamine or a succinimide of alkylene polyamine or
   2. further contacted with a basic calcium compound selected from calcium hydroxide or calcium carbonate.
3. The lubricating composition as defined in claim 1 wherein an aliphatic alcohol is employed to prepare said sulfated alcohol.
4. The lubricating composition as defined in claim 3 wherein said aliphatic alcohol is glycol or glycerol.
5. The lubricating composition as defined in claim 2 wherein an aliphatic alcohol is employed to prepare said sulfated alcohol.
6. The lubricating composition as defined in claim 5 wherein said aliphatic alcohol is glycol or glycerol.

TABLE II

| | Sequence II C Engines Test | | | | | |
|---|---|---|---|---|---|---|
| Inhibitor | Average MW | % ETO | PPM | AER[1] | AER[2] | AER[3] |
| None | — | — | — | 7.1–7.4 | 8.2–8.3 | 6.8 |
| Glycol | 1000 | 10 | 500 | 7.2 | | |
| Glycol-DiSulfate | 1000 | 10 | 500 | 8.9 | 8.6 | 8.2 |
| Glycol-DiSulfate | 1000 | 10 | 200 | 7.1 | | |
| Glycol-DiSulfate | 2000 | 10 | 500 | 8.9 | 8.2–8.3 | |
| Glycol-DiSulfate | 1000 | 10 | 2000 | | | 8.8 |
| Glycerol-Sulfate | 4500 | 14 | 500 | 9.0 | | |
| Glycerol-DiSulfate | 4500 | 14 | 500 | 9.0 | | |
| Glycerol-Sulfate | 4500 | 14 | 200 | 8.9 | | |
| Glycerol-DiSulfate | 4500 | 14 | 200 | 8.7 | | |

[1]Composition A.
[2]Composition B.
[3]Composition C.

UNITED STATES PATENT AND TRADEMARK OFFICE
CERTIFICATE OF CORRECTION

PATENT NO. : 4,046,702
DATED : September 6, 1977
INVENTOR(S) : Thomas V. Liston

It is certified that error appears in the above-identified patent and that said Letters Patent are hereby corrected as shown below:

Column 1, line 37, "amount of a sulfate of a polyoxyalkenated alcohol or phenol is prepared" should read --amount of a sulfate of a polyoxyalkenated alcohol or phenol or sulfate salts thereof, wherein said sulfated alcohol or phenol is prepared--

Column 4, line 65, "The mixture was heated to about 2-1/2 hours." should read --The mixture was heated to about 93°C. for about 2-1/2 hours.--

Column 5, line 50, "550 ppm" should read --500 ppm--.

Column 8, Table I, "Neutralizatin" should read --Neutralization--

Column 10, line 22, "orphenol" should read --or phenol--.

Signed and Sealed this

Twenty-seventh Day of December 1977

[SEAL]

Attest:

RUTH C. MASON
Attesting Officer

LUTRELLE F. PARKER
Acting Commissioner of Patents and Trademarks